(12) United States Patent  (10) Patent No.: US 7,556,609 B2
Scott  (45) Date of Patent: Jul. 7, 2009

(54) MEDICAL AID HAVING A STANDALONE FEMUR TRACTION MODE AND A LEG SUPPORT MODE

(76) Inventor: James W. Scott, 1610 John Orr Dr., Bldg. A, Tifton, GA (US) 31794

( * ) Notice: Subject to any disclaimer, the term of this patent is extended or adjusted under 35 U.S.C. 154(b) by 31 days.

(21) Appl. No.: 11/786,105

(22) Filed: Apr. 11, 2007

(65) Prior Publication Data

US 2008/0255491 A1   Oct. 16, 2008

(51) Int. Cl.
  *A61F 5/00* (2006.01)
(52) U.S. Cl. ............................... 602/32; 602/36
(58) Field of Classification Search ............ 602/5, 602/16, 23, 27; 128/845, 882
  See application file for complete search history.

(56) References Cited

U.S. PATENT DOCUMENTS

| | | | |
|---|---|---|---|
| 439,255 A | 10/1890 | Ruebsam | |
| 2,511,659 A | 6/1950 | Wilson | |
| 3,430,956 A * | 3/1969 | Borgeas | 482/79 |
| 3,661,150 A | 5/1972 | Peterssen et al. | |
| 4,627,423 A * | 12/1986 | Kampner | 602/35 |
| 4,664,099 A | 5/1987 | Pearl, Jr. | |
| 4,664,101 A | 5/1987 | Granberg | |
| 4,998,722 A | 3/1991 | Scott | |
| 5,046,487 A * | 9/1991 | Scott | 601/27 |
| 5,306,231 A | 4/1994 | Cullum et al. | |
| 5,611,770 A * | 3/1997 | Tesch | 601/34 |

\* cited by examiner

*Primary Examiner*—Michael A. Brown
(74) *Attorney, Agent, or Firm*—John P. Sinnott; Langdale Vallotton, LLP

(57) ABSTRACT

A medical aid that functions as (1) a standalone femur traction device for femur traction or (2) a trapezoidally-shaped cushioned leg support pillow. The medical aid can be placed on an ordinary bed and is constructed to provide traction without the use of weights or pulleys. The medical aid includes a base that supports a trapezoidally-shaped leg pillow or support and an adjustable U-shaped fulcrum coupled to the base. The U-shaped fulcrum supports thereon an elastic cord with an attached leg pin connector. Adjustment of the U-shaped fulcrum and/or the tension applied by the elastic cord varies the amount of traction. The trapezoidally-shaped cushioned leg support can be used with or without the base.

24 Claims, 8 Drawing Sheets

MEDICAL AID HAVING A STANDALONE FEMUR TRACTION MODE AND A LEG SUPPORT MODE

CROSS REFERENCE TO RELATED APPLICATIONS

James W. Scott, M.D. Design Patent Application Titled "Femur Traction and Leg Support Apparatus, or the Like, filed of even date herewith.

STATEMENT REGARDING FEDERALLY SPONSORED RESEARCH OR DEVELOPMENT

None

JOINT RESEARCH AGREEMENT PARTNER

None

REFERENCE TO "SEQUENCE LISTING"

None

BACKGROUND OF THE INVENTION

The present invention relates to traction devices and, more particularly, to a medical aid that can function as (1) a standalone femur traction device for femur traction without the use of weights and pulleys and (2) a trapezoidally-shaped cushioned leg support pillow, and the like. Both the traction device and the leg support pillow can be placed on an ordinary bed, gurney or other horizontal surface.

Fractures or surgery of the femur or other bones require traction to prevent contraction of the muscles and other bone displacement. Traction devices are used as part of the medical recovery process to stretch or exercise the muscles. Many of the known traction devices are complex apparatuses which are bolted or otherwise secured to the patient bed and have numerous working parts which can be lost or malfunction. As can be appreciated, these traction devices are expensive and require skilled hospital personnel to install. Furthermore, the complex apparatuses of traction devices are not easily transported and are generally limited to use in a hospital.

Various attempts have been made to simplify the complex apparatus of traction devices.

U.S. Pat. No. 4,627,423, issued to Kampner, titled "PORTABLE TRACTION DEVICE", discloses a self-contained traction device for pelvic or cervical spine traction which can be placed on an ordinary bed. The traction device of Kampner relies on pulleys and weights. The traction device also requires a support leg that extends to the floor for additional support.

U.S. Pat. No. 3,661,150, issued to Peterssen et al., titled "SPLINT FOR THE TREATMENT OF FRACTURED LEGS", discloses a splint for a fractured leg which includes a support for the femur pivotally connected to the femur support and a support for the tibia-fibula. The splint also includes pulleys and weights.

U.S. Pat. No. 4,664,099, issued to Pearl, Jr., titled "TRACTION DEVICE", discloses a traction device for treating a fracture of the femur bone that includes vertical frame with telescopic tubes and horizontal frame having horizontal telescopic tubes. The vertical frame includes cross members which support adjustable spring tensioning devices. One of the spring tensioning devices attaches to a stirrup for attachment to a pin in the patient's leg.

Other traction devices include U.S. Pat. No. 5,306,231, issued to Cullum, et al., titled "TRACTION SYSTEM FOR A PATIENT IN A BED"; U.S. Pat. No. 4,664,101, issued to Granberg, titled "OPEN FRAME TRACTION SYSTEM"; U.S. Pat. No. 2,511,659, issued to Wilson, titled "SURGICAL SPLINT"; and U.S. Pat. No. 439,255 issued to Ruebsam, titled "APPARATUS FOR TREATMENT OF ANKYLOSIS", none of which meet the needs of the present invention.

U.S. Pat. No. 4,998,722, issued to James W. Scott, titled "ISOTONIC EXERCISING APPARATUS", incorporated herein by reference as if set forth in full below, discloses an isotonic exercising apparatus that includes a support pillow for elevating the leg. The support pillow is generally trapezoidally-shaped and includes a series of straps for restraining the leg on top of the pillow.

As can be readily seen, there is a continuing need for a medical aid that functions as a standalone femur traction device that can be placed on an ordinary bed in the hospital or at home and which is lightweight.

Another continuing need is for a standalone femur traction device that requires essentially no installation except the placement on an ordinary bed or other support surface.

A still further need is for a standalone femur traction device that is simple to use and vary the traction level by a patient and healthcare personnel.

A still further need is for a medical aid that functions as removable multi-purpose leg support pillow useable with or without the traction device such as when the patient is transported.

As will be seen more fully below, the present invention is substantially different in structure, methodology and approach from that of prior traction devices or medical aids.

BRIEF SUMMARY OF THE INVENTION

The preferred embodiment of a traction device, medical aid or standalone femur traction device of the present invention generally solves the aforementioned problems in a straight forward and simple manner. The traction device, moreover, need not be removed from the patient's leg, for example, during transport for x-rays or change to a different room and thus can be used to continue traction during transportation by helicopter, ambulance and the like.

Broadly, the present invention contemplates a medical aid that functions as a standalone femur traction device that can be placed on an ordinary bed and which includes a removable multi-purpose leg support pillow. The pillow can be used independently of the traction device.

The present invention further contemplates a standalone femur traction device for femur traction which can be placed on an ordinary bed and is constructed to provide traction without the use of weights or pulleys. The femur traction device includes a base that supports a trapezoidal-shaped leg pillow or support and an adjustable U-shaped frame coupled to the base. The U-shaped frame supports thereon an elastic cord with an attached leg pin connector or stirrup.

In view of the above, an object of the present invention is to provide a femur traction device which varies the amount of traction by adjusting the U-shaped frame with respect to the base and/or the strength of the elastic cord.

A still further object of the present invention is for medical aid that includes a removable leg support pillow usable with or without the traction device such as when the patient is transported.

A further object of the present invention is to provide a medical aid serving as a femur traction device with a removable leg support pillow wherein when traction is no longer needed, the removable leg support pillow can be used as a standalone leg rest for elevating the foot, the ankle or the knee or to relieve pressure from the lower back.

In view of the above, a feature of the present invention is to provide a medical aid that is relatively lightweight, portable and modular.

Another feature of the present invention is to provide a medical aid for femur traction and leg elevation and resting that is compact and can be used in a military environment.

A further feature of the present invention is to provide a medical aid that functions as a femur traction device and which is relatively simple structurally and thus simple to manufacture.

The above and other objects and features of the present invention will become apparent from the drawings, the description given herein, and the appended claims. The scope of the invention being limited only through claims appended hereto.

BRIEF DESCRIPTION OF THE DRAWING

For a further understanding of the nature and objects of the present invention, reference should be had to the following description taken in conjunction with the accompanying drawings in which like parts are given like reference numerals and, wherein.

DETAILED DESCRIPTION OF PREFERRED EMBODIMENT OF THE INVENTION

Figure 1:
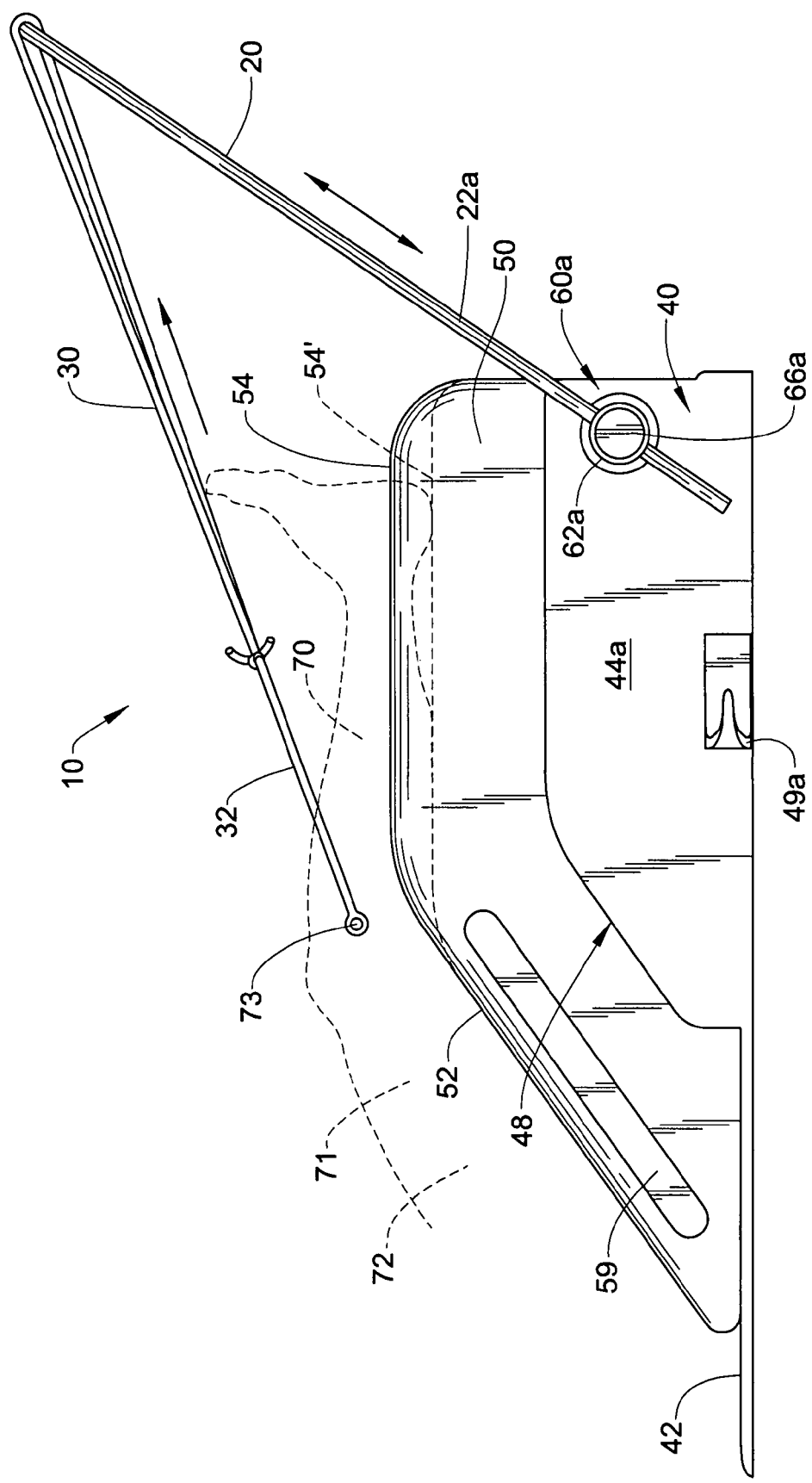
FIG. 1 illustrates a side view of the medical aid functioning as a femur traction device of the present invention employed during traction.

Referring now to the drawings and in particular FIGS. 1-6, a medical aid that functions as a femur traction device 10 of the present invention is generally comprised of an adjustable U-shaped frame 20 supporting an elastic cord 30, a base 40 adjustably supporting the U-shaped frame 20 and a standalone and removable pillow 50. The elastic cord 30 is a flexible and resilient cord having a leg pin connector or stirrup 32 coupled thereto. The leg pin connector or stirrup 32 serves to connect to a pin 73 in the patient's leg 71.

Figure 2:
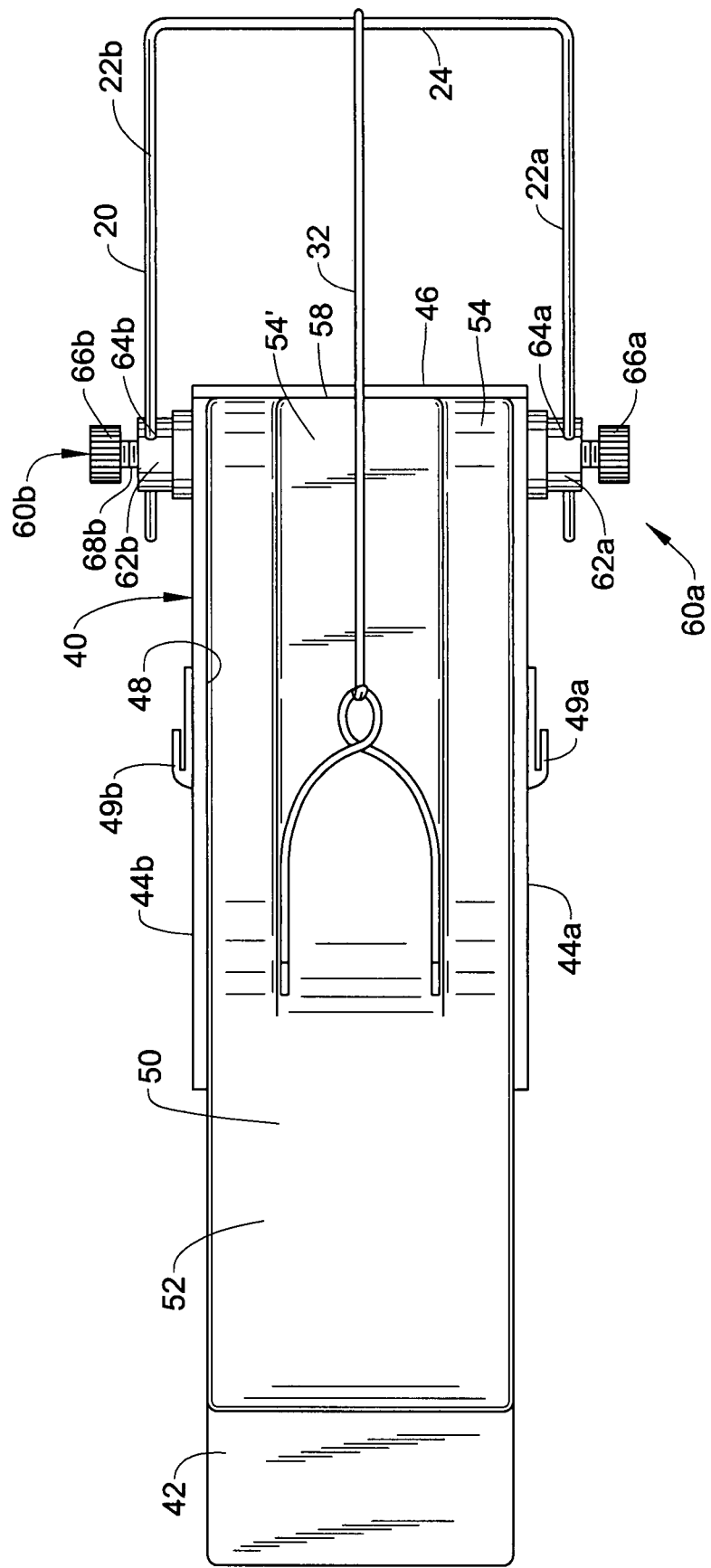
FIG. 2 illustrates a top view of the medical aid functioning as the femur traction device of the present invention shown in FIG. 1.
Figure 3:
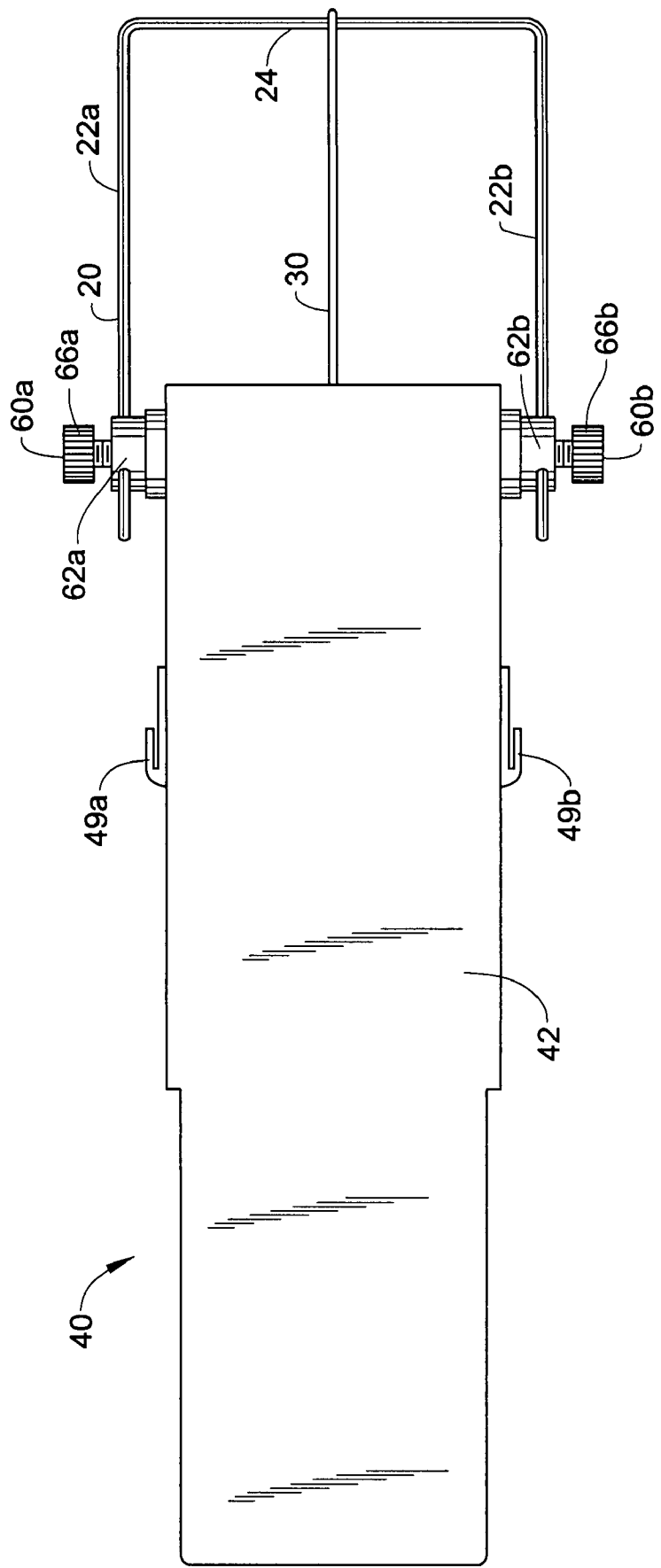
FIG. 3 illustrates a bottom view of the medical aid shown in FIG. 1 functioning as the femur traction device of the present invention.
Figure 6:
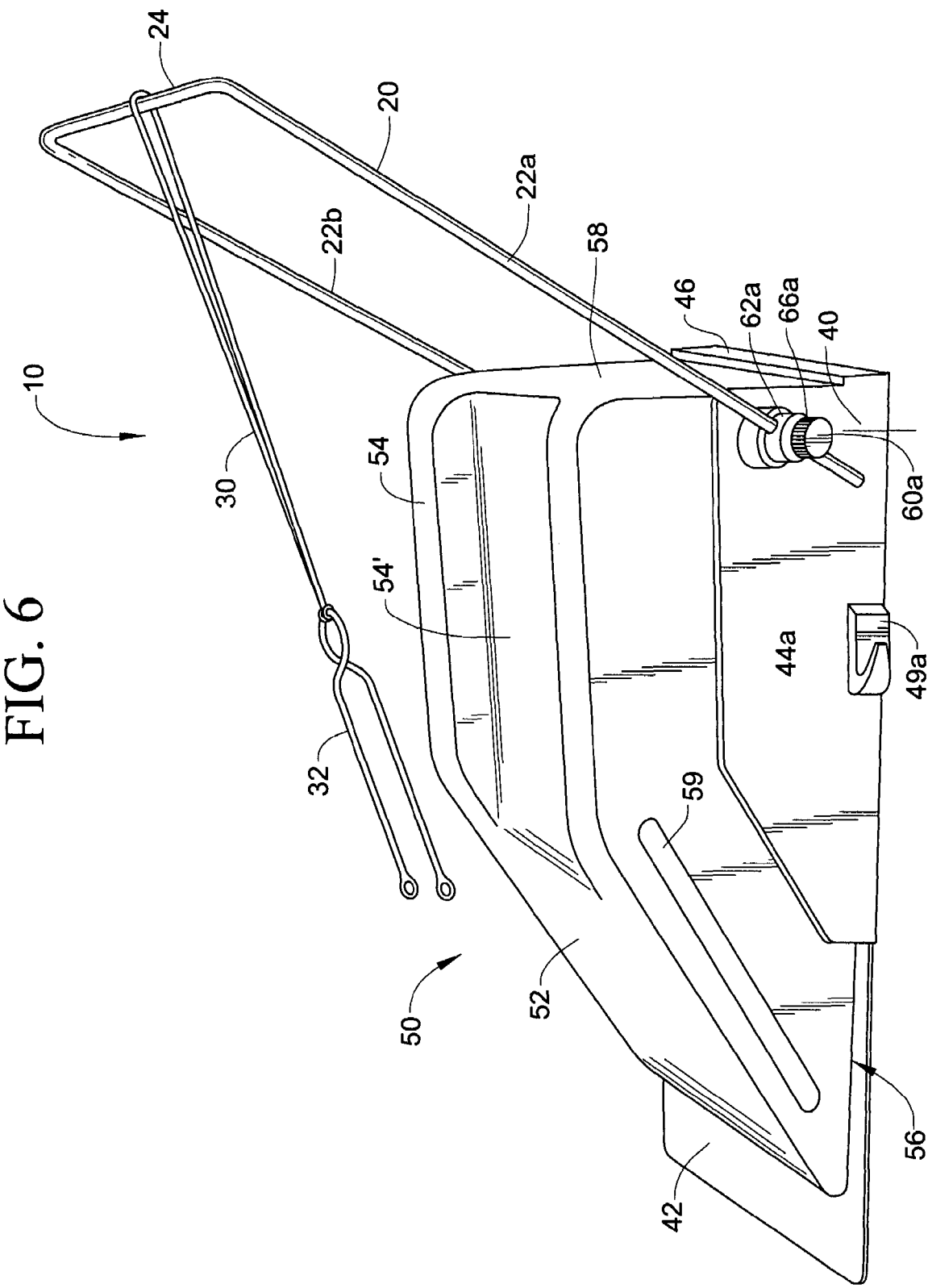
FIG. 6 illustrates a perspective view of the medical aid shown in FIGS. 1 through 5 functioning as the femur traction device of the present invention.

As best seen in FIGS. 2 and 6, the pillow 50 has in its side elevation illustrated in FIG. 6 a trapezoidal-shape defined by an inclined front surface 52, a top horizontal surface 54 with a channel $54^1$ formed therein, a horizontal bottom surface 56 that is longer than the top horizontal surface 54 and a back surface 58. In the exemplary embodiment, the back surface 58 is generally vertical and thus is not parallel with the inclined front surface 52. The pillow 50 includes a bottom flat surface so that it is self-stabilized on a bed, gurney or other horizontal surface.

Figure 4:
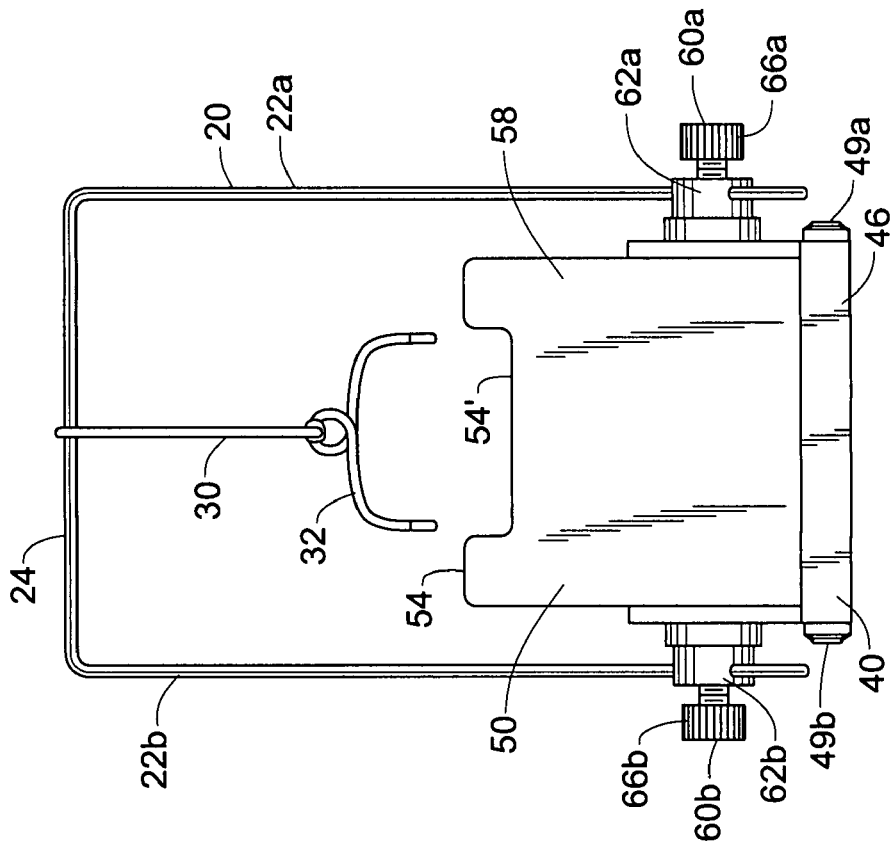
FIG. 4 illustrates a front view of the medical aid shown in FIG. 1 functioning as the femur traction device of the present invention.
Figure 5:
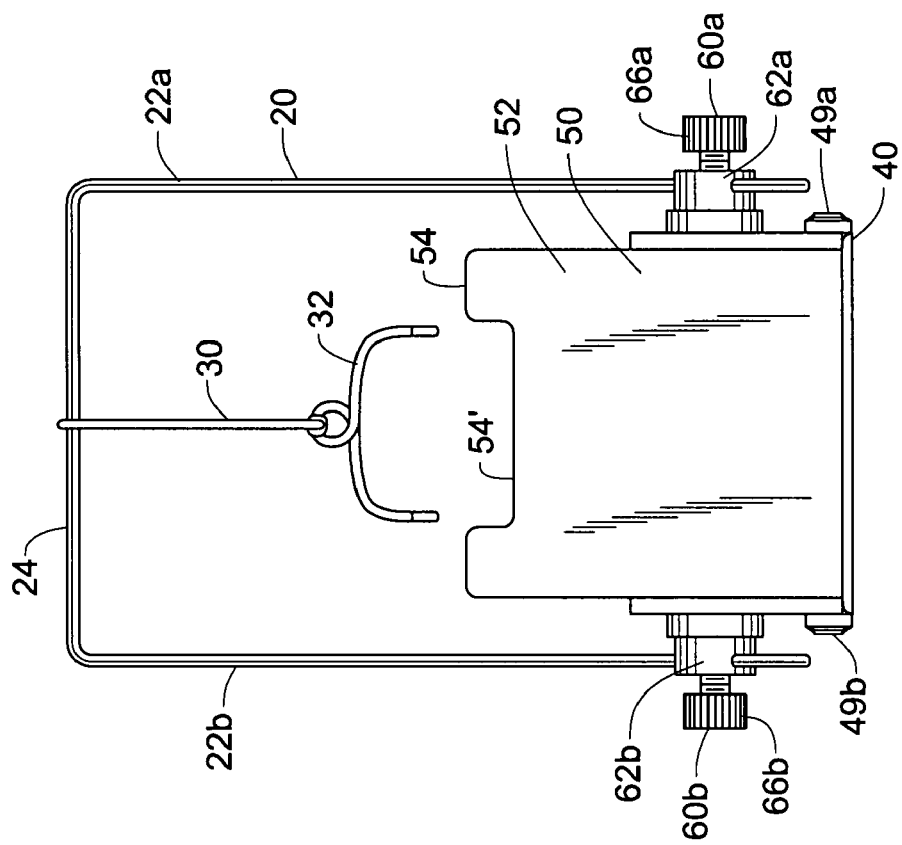
FIG. 5 illustrates a back view of the medical aid shown in FIG. 1 functioning as the femur traction device of the present invention.

The channel $54^1$ creates a low profile U-shaped recess or cradle, as best seen in FIGS. 4 and 5, along the longitudinal center of the top horizontal surface 54 for the placement of the tibia-fibula 70 (FIG. 1) of the patient's leg 71. Thereby, when resting the tibia-fibula 70 in the channel $54^1$, whether for traction or elevation, the leg 71 is prevented from rolling off the pillow 50 inadvertently. The inclined front surface 52 supports femur 72 of the leg 71. The slope of the inclined front surface 52 releases pressure on the lower back by bending and elevating the knee.

In the preferred embodiment, the pillow 50 is made of a solid foam, foam-rubber, closed-cell cushioning material or open-cell cushioning material. The density of the foam or cushioning material should provide resiliency for comfort but also provide sufficient strength to firmly support the leg of a 200-400 lb. patient without the pillow collapsing.

In the preferred embodiment, the pillow 50 is removable from base 40. Therefore, the pillow 50 with or without the base 40 can be used as a standalone leg rest/leg elevator for elevating a foot, an ankle or a knee. Additionally, the standalone leg rest/leg elevator can be used to elevate a leg to relieve pressure from the lower back or spine.

The pillow 50 also includes a channel or elongated recess 59 parallel to the inclined front surface 52. Only one channel or recess 59 is shown. However, both sides of the pillow 50 could include such a channel or recess 59.

As can be appreciated, the traction device 10 can serve in two modes. In the first mode, the traction device 10 applies a predetermined force to an impaired tibia-fibula. In the second mode, the traction device 10 supports, elevates or cushions the patient's leg. The pillow 50, during patient transport, will absorb impact or vibrational forces to minimize pain in the patient's injured leg. A separate view of the standalone pillow is not shown since the other figures clearly depict the details of the pillow.

As described in U.S. Pat. No. 4,998,722, titled "ISO-TONIC EXERCISING APPARATUS", incorporated herein by reference, elevating an injured leg or a leg after surgery can assist in the flow of blood through the leg. Thus, the pillow 50 of the present invention is multi-functional since it can be used with or without the base 40. The trapezoidal shape of the pillow 50 comfortably elevates the patient's leg 71 to aid the flow of blood through the injured leg 71. Furthermore, the femur traction device 10, because it is not secured to a patient's bed, it can be easily removed and placed on a gurney to aid in the support and/or elevation of the leg 71 as a patient is transported. Since the pillow 50 is cushioned during transport such as with a gurney, and as mentioned above, the pillow 50 will absorb at least some of the impact forces or vibrational forces exerted on the gurney as it rolls to minimize the same forces being channeled to the patient's injured leg 71. Likewise, pillow 50 can be used with or without the base 40 (FIG. 3) when transporting a patient via an ambulance or airlift. During transportation, it is preferred that the leg pin connector or the stirrup 32 (FIG. 1) is not connected to the patient, if the base and pillow are kept together. Even when traction is no longer needed for the injury, the patient may need to elevate the leg 71 from time to time, and the pillow 50 serves such a function.

As illustrated, the base 40 includes a bottom panel 42 (FIG. 3), two side panels 44a and 44b (FIG. 2), perpendicularly coupled to respective sides of bottom panel 42 and a rear flange 46 (FIG. 5). The area between the two side panels 44a and 44b (FIG. 2) and rear flange 46 creates a discrete pillow placement cavity 48 for defining the placement of and supporting the pillow 50 when performing traction. In the preferred embodiment, the back surface 58 (FIG. 2) of the pillow 50 abuts the rear flange 46. The width of the pillow 50 is slightly less than the distance between the interior surfaces of the two side panels 44a and 44b. The length of the horizontal bottom surfaces 56 (FIG. 6) is less than bottom panel 42.

The base also includes a pair of hooks 49a and 49b (FIG. 2) on the side panels 44a and 44b, respectively. The hooks 49a and 49b can be used to temporarily attach the traction device 10 to a bed, gurney or the like by means of an elastic cord (not shown). The two ends of the cord each can be secured to a respective one of the hooks 49a and 49b after the cord has been passed under the mat, bed springs or other supporting structure.

The femur traction device 10 further includes adjustable frame-to-base connectors 60a and 60b (FIG. 2) coupled through the side panels 44a and 44b, respectively, to the base 40. The frame-to-base connectors 60a and 60b include collars 62a and 62b and knobs 66a and 66b, respectively. Collars 62a and 62b include through holes 64a and 64b adapted to receive therein respective parallel legs 22a, 22b of the U-shaped frame 20.

The U-shaped frame 20 further includes a crossbar 24 having distal ends perpendicularly coupled to parallel legs 22a and 22b. The height of the U-shaped frame 20 and, more specifically the height of the crossbar 24, can be adjusted by sliding the parallel legs 22a and 22b up or down in the through holes 64a and 64b.

Figure 7:
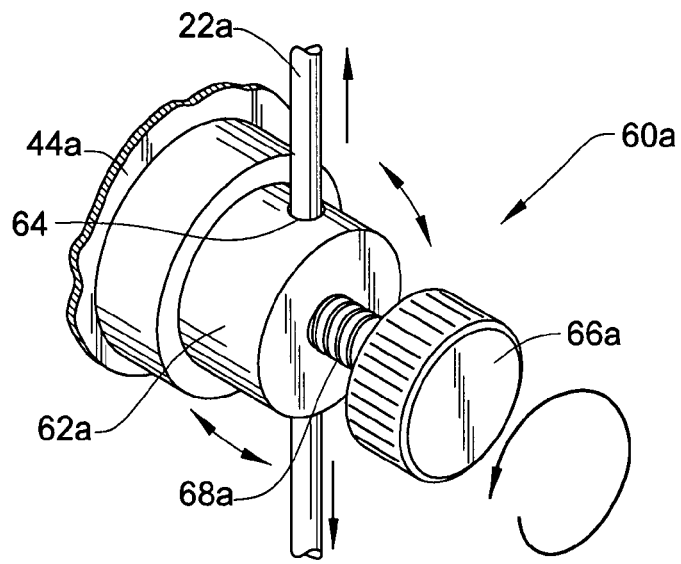
FIG. 7 illustrates a perspective view of the adjustable frame-to-base connector of the present invention.

Referring now to FIG. 7, the frame-to-base connector 60a for the side panel 44a is shown and FIG. 2 shows the similarly constructed companion frame-to-base connection 60b for the side panel 44b. Knobs 66a and 66b each have a respective threaded rod or pin 68a and 68b coupled thereto. Each threaded rod or pin 68a and 68b is received in a threaded hole in a respective one of collars 62a, 62b. Tightening knobs 66a and 66b selectively secures or lock collars 62a and 62b and the associated legs 22a and 22b in a predetermined angular relation and linear separation relative to the pillow 50 as best shown in phantom or broken lines in FIG. 8.

The U-shaped frame 20 acts as the fulcrum for the traction and is adjustable longitudinally by loosening the knobs 66a and 66b, moving the U-shaped frame 20 either up or down through holes 64a and 64b in collars 62a and 62b and then re-tightening the knobs 66a and 66b. The U-shaped frame 20 is oriented above the plane of the patient's leg 71.

Figure 8:
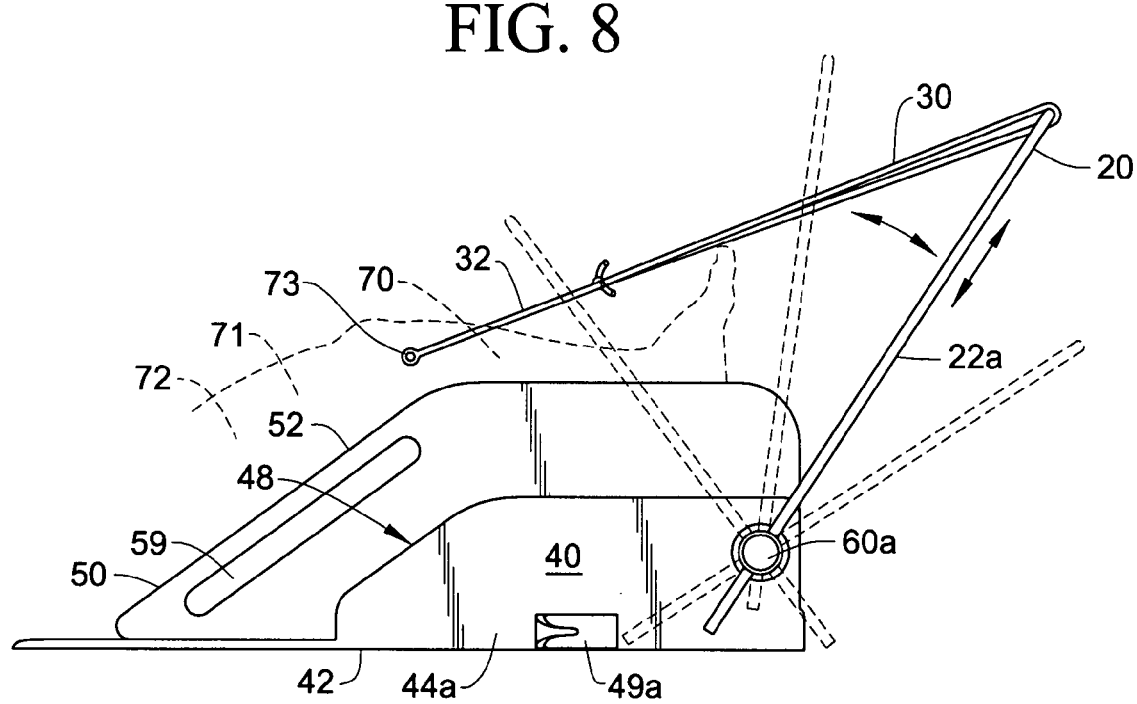
FIG. 8 is a side view of the medical aid shown in FIG. 1 illustrating the variability of the U-shaped fulcrum of the present invention.

As best seen in FIG. 8, the angle of the U-shaped frame 20 with respect to the bottom panel 42 can be adjusted. In other words, the adjustable feature of the U-shaped frame 20 also allows the U-shaped frame 20 to be rotated or pivoted toward or away from the patient by loosening the same knobs 66a and 66b, rotating the same collars 62a and 62b and then re-tightening the knobs 66a and 66b.

In the exemplary embodiment, the U-shaped frame 20 comprises a metal cylindrical rod bent approximately 90 degrees to form the two parallel support legs 22a and 22b and crossbar 24 (FIG. 2).

The degree of traction can also be varied by changing the length and tension applied to the elastic cord 30, varying the height of the U-shaped frame 20 and/or varying the angle of the U-shaped frame 20 with respect to the bottom panel 42. As can be appreciated, the variability also allows the femur traction device 10 to accommodate a wide range of adult leg sizes, including a wide range of tibia-fibula lengths. An advantage of the present invention is that with very little adjustment in the U-shape frame 20 or use of a different elastic cord 30, the femur traction device 10 is a one-size fits all (adult) device. Children would require a smaller or lower-profile pillow height to accommodate for the length of their femur.

The operation of the femur traction device 10 is relatively simple. To begin traction, the foot and tibia-fibula 70 of the patient's leg 71 is placed or rested in channel $54^1$, as best seen in FIGS. 1 and 8. Thereafter, the leg pin connector or stirrup 32 is connected to a pin 73 in the patient's leg 71.

Since the same size pillow 50 is used for all heights of adult patients, the foot of the taller patient may extend beyond the pillow 50. Nevertheless, the distance to the pin 73 in a patient's knee would, in general, be the same since the knee bends about the contour of the obtuse angle defined by the inclined front surface 52 and the channel $54^1$ formed in the top horizontal surface 54.

Prior to traction, the degree of traction may be adjusted by changing the elastic cord 30 applying a predetermined tension to the cord 30, lowering or raising the height of the U-shaped frame 20 and/or adjusting the angle of the U-shaped frame 20 with respect to the bottom panel 42. As can be appreciated, changing the resiliency or length of the elastic cord 30 also will modify the degree of traction.

Once the desired degree of traction is established, the patient can easily connect and reconnect the leg pin connector or stirrup 32 to the pin 73.

In the exemplary embodiment, the elastic cord 30 is a bungee cord. Nevertheless, other various types of leg pin connectors or stirrups can be used to accommodate different pin ends.

Figure 9:
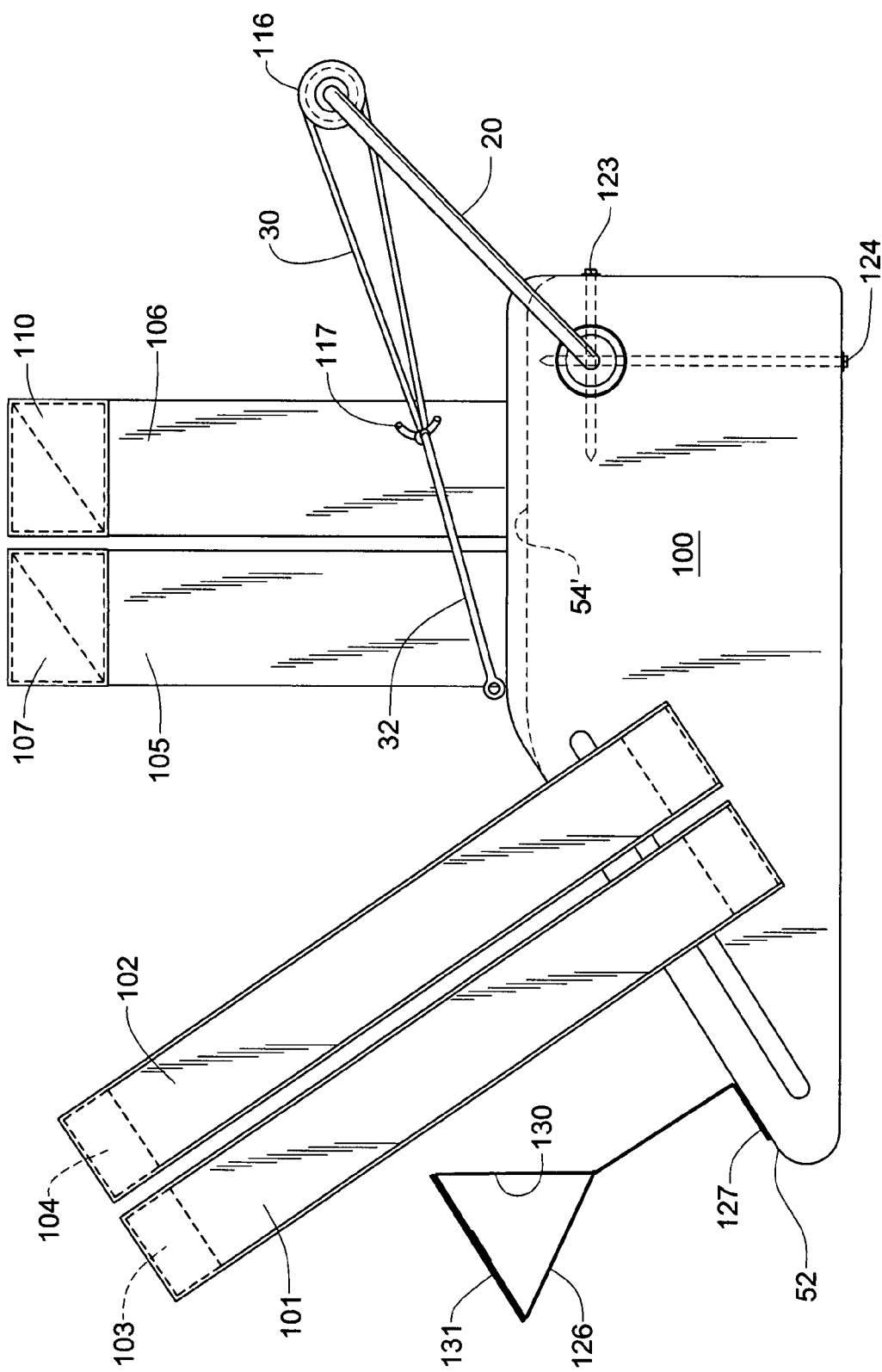
FIG. 9 is a side elevation of the traction device that discloses another embodiment of the invention.
Figure 10:
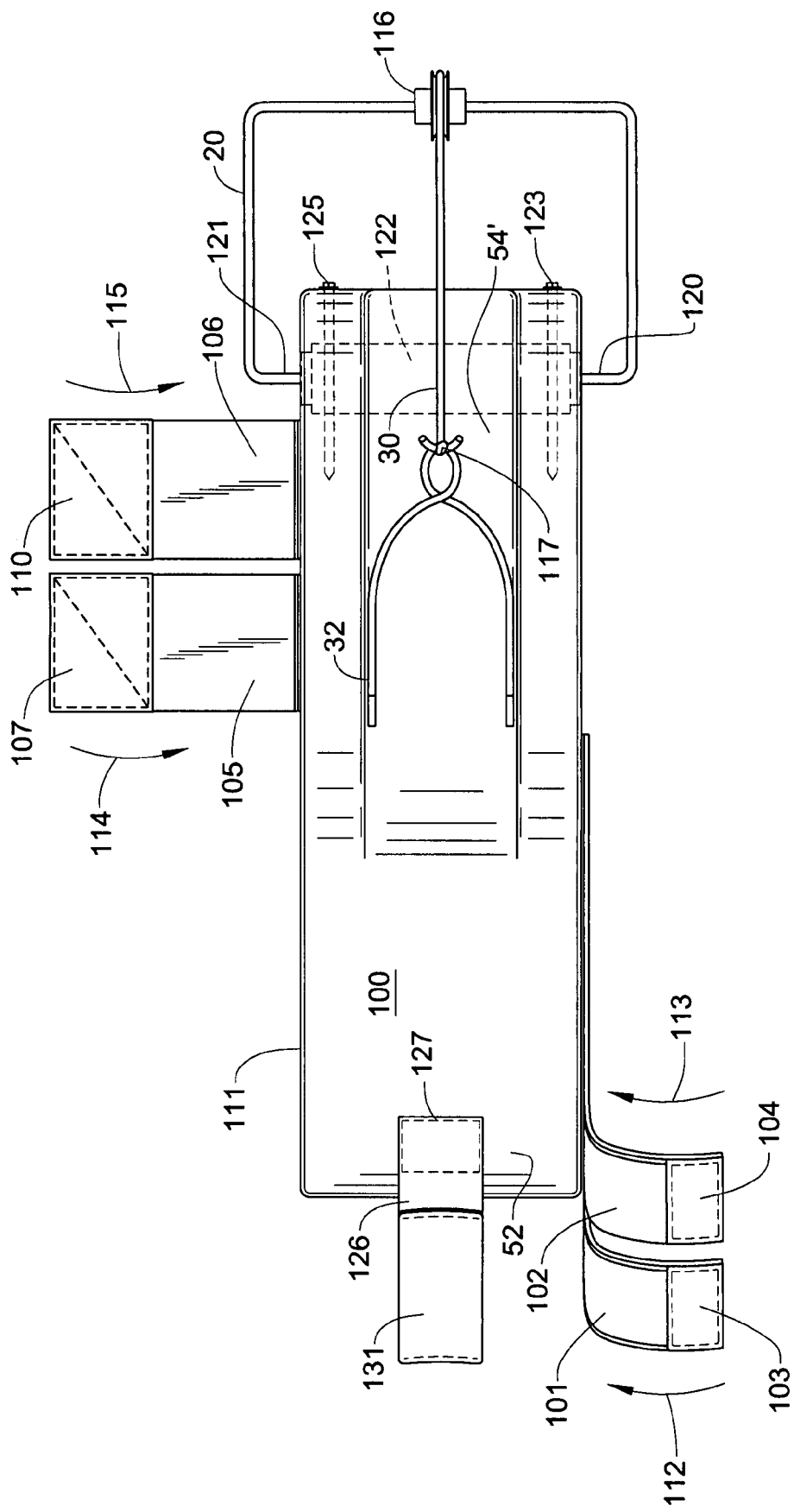
FIG. 10 is a plan view of the embodiment of the invention shown in FIG. 9.

A further embodiment of the standalone traction device is shown in FIGS. 9 and 10. As illustrated, a resilient pillow 100 has a generally trapezoidal profile. Straps 101, 102 are stitched or otherwise are secured to the trapezoidal side of the pillow 100 that is shown in FIG. 9. These straps 101, 102, moreover, are provided with Velcro, or other suitable fasteners 103, 104 on their respective ends to releasably retain the patient's thigh (not shown in FIG. 9) against the inclined front surface 52 of the pillow 100.

Another set of straps 105, 106 also having Velcro or other suitable fasteners 107, 110 affixed to pillow side 111 (FIG. 10) can be passed over the patient's calf and secured to the trapezoidal surface of the pillow 100 shown in FIG. 9 in order to releasably secure the patient's calf (not shown in FIG. 9) in the channel $54^1$. Attention is invited to the plan view of the pillow 100 shown in FIG. 10 wherein the straps 101, 102 are drawn transversely across the inclined front surface 52 of the pillow 100 in the direction of arrows 112, 113. The respective fasteners 103, 104 are pressed against the pillow side 111 temporarily to keep the patient's thigh immobilized against the inclined surface 52.

In a similar manner, the fasteners 107, 110 associated with the straps 105, 106 are drawn in the direction of respective arrows 114, 115 to immobilize the patient's calf in the channel $54^1$.

Traction in an appropriate predetermined amount selectively is applied to the patient's injured limb by the stirrup 32 which is fastened to the elastic cord 30. As best illustrated in FIG. 9, moreover, is a structure for securing the elastic cord 30 to the stirrup 32. The elastic cord 30 passed around a sheave 116 (FIG. 9) that is rotatably received on the U-shaped frame 20. Both of the ends of the elastic cord 30 are knotted 117 or otherwise secured to the central portion of the stirrup 32 after the desired degree of tension is established between the stirrup 32 and the sheave 116 through the elastic cord 30, the angular orientation of the frame 20 relative to the pillow 100, or both.

Turning to FIG. 10, it can be seen that the U-shaped frame 20 has a pair of inwardly turned ears 120, 121 that each are received in opposite ends of a mounting 122 within the pillow 100. A set of perpendicularly oriented screws 123, 124 (FIG. 9) penetrate adjoining sides of the pillow 100 and one end of the mounting 122 to fix the mounting 122 in place. Note that a corresponding set of screws, of which only the screw 125 is shown in FIG. 10 secure the opposite end of the mounting 122 in the pillow 100.

A further strap 126 is joined to the inclined surface 52 of the pillow 100 through stitching 127 or the like. As illustrated in FIG. 9, the fabric that forms the strap 126 is doubled over on itself to form a loop or a passageway 130 to accommodate a further, transversely oriented strap or belt (not shown in the drawing) to enable the patient's thigh and the traction device to be temporarily attached to some other structure, e.g. a gurney or a hospital bed. In this manner, the entire traction apparatus is capable not only of independent movement, but also for use as an essentially permanent injured leg or back support apparatus within a hospital or sick-room.

Attention is further invited to an erasable writing surface 131 that is joined to the exposed side of the strap 126. Thus, information specific to the patient can be entered on the writing surface.

Individual elements of the various embodiments of the invention, as described above, are interchangeable. For example, the sheave 116 and its associated tensioning equipment shown in FIGS. 9 and 10 can be substituted for the U-shaped frame 20 and its associated structure shown in FIG. 8. Conversely, the frame-to-base connectors 60a and 60b illustrated in FIGS. 2, 7 and 8 can be substituted for the mounting 122 and the ears 120, 121 that characterize the embodiment of the invention shown in FIGS. 9 and 10.

Because many varying and differing embodiments may be made within the scope of the inventive concept herein taught and because many modifications may be made in the embodiment herein detailed in accordance with the descriptive requirement of the law, it is to be understood that the details herein are to be interpreted as illustrative and not in a limiting sense.

What is claimed is:

1. A tibia-fibula leg standalone traction device for use with a leg pin connector comprising: a base adapted to be placed on a generally flat surface and having a discrete pillow placement cavity; a trapezoidally-shaped pillow adapted to be received and supported in said discrete pillow cavity; a U-shaped fulcrum adjustably coupled to said base and which extends upward above the plane of said trapezoidally-shaped pillow; and an elastic cord supported by said U-shaped fulcrum and which is adapted to support the leg pin connector.

2. The device of claim 1, wherein said trapezoidally-shaped pillow is made of a dense cushioning material.

3. The device of claim 1, wherein said pillow comprises: an inclined surface; a surface having a channel formed therein for cradling the tibia-fibula of a leg; a surface spaced from and longer than said channel surface; and another surface generally perpendicular to said channel surface and said surface spaced therefrom.

4. The device of claim 1, wherein said pillow is removable from said base.

5. The device of claim 1, wherein said U-shaped fulcrum has an adjustable height.

6. The device of claim 1, wherein said U-shaped fulcrum has an adjustable angle with respect to said base.

7. The device of claim 1, wherein said U-shaped fulcrum has an adjustable height and an adjustable angle with respect to said base.

8. The device of claim 1, wherein said base comprises: a panel adapted to lie on said generally flat surface; a first and second side walls coupled perpendicularly to said panel; and a flange protruding perpendicularly from said panel and said first and second side walls wherein said first and second side walls and said rear flange form said discrete pillow placement cavity.

9. The device of claim 8, further comprising first and second said fulcrum adjusters coupled to said first and second side walls, respectively, for adjusting at least one of a height and an angle of said U-shaped fulcrum.

10. A femur standalone traction device for use with a leg pin connector comprising: an adjustable U-shaped fulcrum supported by a base, said base adapted to be placed on a generally flat surface; an elastic cord supported by said U-shaped fulcrum and which is adapted to support the leg pin connector; and a standalone and removable trapezoidally-shaped pillow adapted to be received and supported by said base, said pillow forming a cradle for the femur.

11. The device of claim 10, wherein said trapezoidally-shaped pillow is made of a dense cushioning material.

12. The device of claim 10, wherein said pillow comprises: an inclined surface; a surface having formed therein said femur cradle; a surface spaced from and longer than said femur cradle surface; and a further surface generally perpendicular to said femur cradle surface and said surface spaced therefrom and thus not parallel with said inclined surface.

13. The device of claim 10, wherein said adjustable U-shaped fulcrum has an adjustable height.

14. The device of claim 10, wherein said adjustable U-shaped fulcrum has an adjustable angle with respect to said base.

15. The device of claim 10, wherein said adjustable U-shaped fulcrum has an adjustable height and an adjustable angle with respect to said base.

16. The device of claim 10, wherein said base comprises: a panel adapted to lie on said generally flat surface; a first and second side walls protruding perpendicularly to said panel; and a rear flange protruding perpendicularly from said panel and said first and second side walls wherein said first and second side walls and said rear flange form a discrete pillow placement cavity for said removable trapezoidally-shaped pillow.

17. The device of claim 16, further comprising first and second said fulcrum adjusters coupled to said first and second side walls, respectively, for adjusting at least one of a height and an angle of said U-shaped fulcrum.

18. A multi-mode medical traction aid for an injured leg with a pin therein comprising a trapezoidally-shaped pillow for supporting and elevating the injured leg, said pillow forming a cradle for the injured leg, a frame, a mounting secured to said pillow for adjusting the position of said frame relative to said pillow a stirrup for coupling to the pin, and an elastic cord for coupling said stirrup to said frame and to establish with said frame position relative to said pillow a predetermined tension to selectively apply an appropriate traction through the pin to the injured leg.

19. The medical aid of claim 18, wherein said pillow is made of dense cushioning material to absorb vibrational and impact forces when a patient is being transported.

20. The device of claim 18, wherein said pillow comprises: an inclined surface, a surface with a channel formed therein for forming a cradle for the injured leg, a surface spaced from said channel surface and longer than said channel surface, and another surface generally perpendicular to said channel surface and said surface spaced therefrom.

21. The device of claim 18 further comprising a sheave mounted on said frame for receiving said elastic cord.

22. The device of claim 18 further comprising a plurality of straps disposed generally transversely to said pillow cradle.

23. The device according to claim 18 further comprising fastening means on said straps in said plurality thereof to releasably secure said straps to said pillow.

24. The device according to claim 18 further comprising ears on said frame, said ears being inwardly turned toward each other, said mounting receiving said ears to support said frame on said pillow.

* * * * *